US011857630B2

(12) United States Patent
Sill et al.

(10) Patent No.: US 11,857,630 B2
(45) Date of Patent: *Jan. 2, 2024

(54) FORMULATIONS OF SN-38 WITH POLY(AMINO ACID) BLOCK POLYMERS

(71) Applicant: Tyndall Formulation Services, LLC, Tampa, FL (US)

(72) Inventors: Kevin N. Sill, Tampa, FL (US); Bradford T. Sullivan, Clearwater, FL (US)

(73) Assignee: TYNDALL FORMULATION SERVICES, LLC, Tampa, FL (US)

(*) Notice: Subject to any disclaimer, the term of this patent is extended or adjusted under 35 U.S.C. 154(b) by 208 days.

This patent is subject to a terminal disclaimer.

(21) Appl. No.: 17/142,757

(22) Filed: Jan. 6, 2021

(65) Prior Publication Data
US 2021/0213132 A1 Jul. 15, 2021

Related U.S. Application Data

(60) Provisional application No. 62/959,639, filed on Jan. 10, 2020.

(51) Int. Cl.
A61K 47/34 (2017.01)
A61K 9/08 (2006.01)
A61K 9/19 (2006.01)
A61K 31/4375 (2006.01)
A61K 31/513 (2006.01)
A61K 31/519 (2006.01)
A61K 45/06 (2006.01)
A61K 47/26 (2006.01)

(52) U.S. Cl.
CPC ............... A61K 47/34 (2013.01); A61K 9/08 (2013.01); A61K 9/19 (2013.01); A61K 31/4375 (2013.01); A61K 31/513 (2013.01); A61K 31/519 (2013.01); A61K 45/06 (2013.01); A61K 47/26 (2013.01)

(58) Field of Classification Search
CPC ..................... C08G 81/02; A61K 31/337
See application file for complete search history.

(56) References Cited

U.S. PATENT DOCUMENTS

| | | | |
|---|---|---|---|
| 2,671,772 A | 3/1954 | MacDonald | |
| 7,799,339 B2 | 9/2010 | Sill et al. | |
| 8,980,326 B2 | 3/2015 | Sill et al. | |
| 9,078,930 B2 | 7/2015 | Sill et al. | |
| 10,836,869 B1* | 11/2020 | Sill | ........ C08G 81/028 |
| 10,918,619 B1 | 2/2021 | Sill et al. | |
| 11,286,344 B2* | 3/2022 | Sill | ........ C08G 69/10 |
| 2008/0274173 A1 | 11/2008 | Sill | |
| 2018/0228796 A1* | 8/2018 | Sill | ........ A61K 47/26 |
| 2021/0214496 A1 | 7/2021 | Sill | |

FOREIGN PATENT DOCUMENTS

| | | | |
|---|---|---|---|
| EP | 2660255 | 11/2013 | |
| EP | 3266456 | 1/2018 | |
| WO | WO-02058622 A2 * | 8/2002 | ....... A61K 47/48815 |
| WO | WO2004017940 | 3/2004 | |
| WO | WO2005117833 | 12/2005 | |
| WO | WO2008134731 | 11/2008 | |

OTHER PUBLICATIONS

Adams, et.al. "Amphiphilic Block Copolymers for Drug Delivery" Journal of Pharmaceutical Sciences, 92(7)1343-1355(2003).
Armstrong, "The occurrence, induction, specificity and potential effect of antibodies against poly (ethylene glycol)," PEGylated Protein Drugs: Basic Science and Clinical Applications, Birkhäuser Verlag/Switzerland, pp. 147-168 (2009) (22 pages).
Arnould, et al., "Meganuclease fusion proteins and their use in targeted integration of transforming DNA," Caplus, 2003:757845 (2020) (2 pages).
Bae, et al., "Oil-encapsulating PEO-PPO-PEO/PEG shell crosslinked nanocapsules for target-specific delivery of paclitaxel," Biomacromolecules, 8(2):650-656 (2007).
Birke, et al., "Polypeptoid-block-polypeptide Copolymers: Synthesis, Characterization, and Application of Amphiphilic Block Copolypept(o)ides in Drug Formulations and Miniemulsion Techniques," Biomacromolecules, 15(2):548-557 (2014).
Birke, et al., "Polysarcosine-containing copolymers: Synthesis, characterization, self-assembly, and applications, " Progress in Polymer Science, 81:163-208 (2018).
Chan, et al., "Polypeptoid polymers: Synthesis, characterization, and properties," Biopolymers, 109(1):e23070 (2018).
Chen, et al., "Gold Nanoparticles Coated With Polysarcosine Brushes to Enhance Their Colloidal Stability and Circulation Time in Vivo," Journal of Colloid and Interface Science, 483:201-210 (2016).
Ferrari, "Cancer Nanotechnology: Opportunities and Challenges," Nature Reviews, 5(3):161-171 (2005).
Fetsch, et al., "Polypeptoids from N-Substituted Glycine N-Carboxyanhydrides: Hydophilic, Hydrophobic, and Amphiphilic Polymers with Poisson Distribution," Macromolecules, 44:6746-6758 (2011).
Ford, et al., Nucleic acids and their encoded polypeptides from human bone marrow, Caplus, 2001:661557:(2020).
Fournier, et al. "A Novel One-Step Drug-Loading Procedure for Water-Soluble Amphiphilic Nanocarriers," Pharmaceutical Research, 21(6):962-968 (2004).
Hamaguchi, et al., "NK105, a Paclitaxel-Incorporating Micellar Nanoparticle Formulation, Can Extend in Vivo Antitumor Activity and Reduce the Neurotoxicity of Paclitaxel," British Journal of Cancer, 92:1240-1246 (2005).

(Continued)

Primary Examiner — Theodore R. Howell
Assistant Examiner — George W Kosturko
(74) Attorney, Agent, or Firm — HALEY GUILIANO LLP; James F. Haley, Jr.; Stacey W. Chung

(57) ABSTRACT

This disclosure relates to the field of formulations of SN-38 with a poly(amino acid) copolymer and methods of making and using thereof. Compositions herein are drug products suitable for the treatment of cancer.

36 Claims, No Drawings

(56) References Cited

OTHER PUBLICATIONS

Heusmann, "A head-to-head comparison of poly(sarcosine) and poly(ethyleneglycol) in peptidic, amphiphilic block copolymers" Polymer 67:240e248 (2015).

Hu, et al., "Polysarcosine as an Alternative to PEG for Therapeutic Protein Conjugation," Bioconjugate Chemistry, 29(7):2232-2238 (2018).

Keck, et al., "Computer method and apparatus for classifying objects such as protein sequences and its application with cyclic peptides osteogenic modulators of bone morphogenetic protine-7," Caplus, 2004:485563 (2020) (2 pages).

Nishiyama, Nanomedicine: Nanocarriers Shape Up for Long Life, Nature Nanotechnology, 2(4):203-204 (2007).

Rios-Doria, et al., "A Versatile Polymer Micelle Drug Delivery System for Encapsulation and In Vivo Stabilization of Hydrophobic Anticancer Drigs," Journal of Drug Delivery, 2012 (8 pages) (2012).

Sill, et al., "Synthesis and Characterization of Micelle-Forming PEG-Poly(Amino Acid) Copolymers With Iron-Hydroxamate Cross-Linkable Blocks for Encapsulation and Release of Hydrophobic Drugs," Biomacromolecules, 18(6):1874-1884 (2017).

Sparreboom, et al., "Comparative Preclinical and Clinical Pharmacokinetics of a Cremophor-Free, Nanoparticle Albumin-Bound Paclitaxel (ABI-007) and Paclitaxel Formulated in Cremphor (Taxol)," Clinical Cancer Research, 11(11):4136-4143 (2005).

Torchilin, "Structure and Design of Polymeric Surfactant-Based Drug Delivery Systems," 73:(2-3):137-172 (2001).

Varlas, et al., "Poly(sarcosine)-Based Nano-Objexts with Multi-Protease Resistance by Aqueous Photoinitiated Polymerization-Induced Self-Assembly" Biomacromolecules, 19(11):4453-4462 (2018).

Viricel, et al., "Monodisperse polysarcosine-based highly-loaded antibody-drug conjugates" Chemical Science, 10(14):4048-4053 (2019).

Weber, et al., "Polysarcosine-Based Lipids: From Lipopolypeptoid Micelles to Stealth-Like Lipids in Langmuir Blodgett Monolayers," Polymers, 8(12):427 (2016) (14 pages).

Weber, et al., "Solution Properties of Polysarcosine: From Absolute and Relative Molar Mass Determinations to Complement Activation" Macromolecules, 51:2653-2661 (2018).

\* cited by examiner

FORMULATIONS OF SN-38 WITH POLY(AMINO ACID) BLOCK POLYMERS

CROSS-REFERENCE TO RELATED APPLICATION

This application claims the benefit under 35 U.S.C. § 119(e) of U.S. Provisional Patent Application No. 62/959,639, filed Jan. 10, 2020. The content of which is incorporated by reference in its entirety.

FIELD OF THE DISCLOSURE

This disclosure relates to the field of formulations of SN-38 and a poly(amino acid) copolymer and methods of making and using thereof.

BACKGROUND OF THE DISCLOSURE

Irinotecan is a chemotherapeutic agent in the camptothecin class of antineoplastic drugs. Irinotecan itself is a prodrug that is hydrolyzed by endogenous carboxylesterases to the active metabolite SN-38 (7-ethyl-10-hydroxycamptothecin) in the liver. SN-38 is a potent topoisomerase I inhibitor which halts DNA replication and promotes cell death. The affinity of the carboxylesterases, specifically CES1 and CES2, for irinotecan is low and it is estimated that less than 10% of the prodrug is hydrolyzed to SN-38 (see: Rivory, L. P. et al. *Biochem. Pharmacol.*, 1996, 52(7), 1103-1111). Additionally, variability in carboxylesterase activity among patients results in different amounts of SN-38 generated from an identical irinotecan dose, and consequently produces a wide range of responses and toxicities. Accordingly, it would be desirable to dose SN-38 directly, allowing for the elimination of variability due to disparate carboxylesterase activities.

Camptosar® (Irinotecan HCl) was approved by the U.S. Food and Drug Administration (FDA) in 1996 for the treatment of colon or rectum cancer. Subsequently, Onivyde®, a liposomal formulation of irinotecan, was developed and approved in 2015 for the treatment of pancreatic cancer. Both of these formulations suffer from the aforementioned problems with administering irinotecan.

The major toxicities associated with irinotecan are severe, delayed onset diarrhea and neutropenia. These toxicities are associated with systemic exposure to SN-38, which is 100 to 1000-fold more potent than irinotecan. SN-38 is inactivated and eliminated from the body via glucuronidation to form SN-38-glucuronide, which is considerably more water soluble and is predominately excreted by the renal route. This reaction is catalyzed by uridine diphosphate glucuronosyltransferase (UGT) expressed in the liver and gastrointestinal tract. UGT is a super family of enzymes encoded by the UGT1A1 genes and at least nine functional isoforms exist. The risk of SN-38-associated toxicity increases with genetic variants of UGT1A1 that reduce the activity of UGT enzymes, the most prevalent being UGT1A1*28 (see: Kweekel, D. *Cancer Treat. Rev.* 2008, 34(7), 656; Gupta, E. et al *Cancer Res.* 1994, 54, 3723.; Hu, Z. Y. et al. *Cancer* 2010, 46, 1856). Approximately 10% of the North American population are homozygous and thus carry two copies of this allele (UGT1A1 *28/*28). Pharmacogenetic studies have established an association between patients homozygous for UGT1A1*28 and an increased risk for hematologic toxicity and/or diarrhea (see: Innocenti, F. et al. *J Clin. Oncol.* 2004, 22, 1382; Routis, E. et al. *Clin. Cancer Res.* 2004, 10, 5151; Ando, Y. et al. *Cancer Res.* 2000, 60, 6921). A study of 95 metastatic colorectal cancer patients treated with irinotecan examined the UGT1A1 genotype-associated toxicities (see: Marcuello, E. et al. *Br. J. Cancer* 2004, 91, 678). The results, presented in Table 1, demonstrate that the incidents of

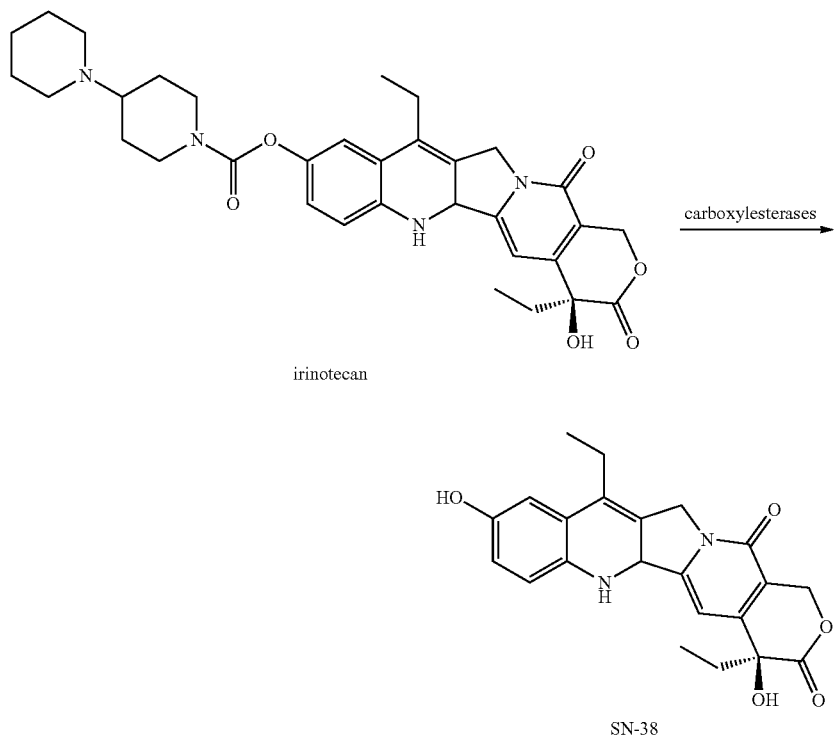

asthenia, diarrhea, and neutropenia toxicities are directly correlated to those carrying one or two *28 alleles.

TABLE 1

Percentage of Patients Experiencing Irinotecan Toxicity by UGT1A1 Genotype

|  | Asthenia | Diarrhea | Neutropenia |
| --- | --- | --- | --- |
| UGT1A1 *1/*1 | 25% | 17% | 15% |
| UGT1A1 *1/*28 | 38% | 33% | 27% |
| UGT1A1 *28/*28 | 70% | 70% | 40% |

Consequently, in 2005 the product information for irinotecan was updated to include a lower starting dose for patients with the UGT1A1 *28/*28 genotype. As discussed previously, variability in the activity of the carboxylesterases responsible for hydrolyzing irinotecan leads to disproportionate amounts of SN-38 among patients receiving an identical dose. This variability exacerbates the SN-38-associated toxicities which are a consequence of UGT1A1 polymorphisms. Hence, the administration of SN-38 directly would allow a physician to assess the UGT1A1 genotype of a patient and personalize the dose of SN-38 to better control the associated toxicities.

SN-38 is extremely insoluble in aqueous media which has hindered development of a formulation that delivers it directly. Synthetic polymers excipients are an attractive option to formulate such hydrophobic active pharmaceutical ingredients (APIs). Poly(ethylene glycol) (PEG), poly(lactic acid) (PLA), poly (lactic acid-co-glycolic acid) (PGLA), and cyclodextrins (CD) are a non-limiting list of examples of polymer excipients that are routinely used in pharmaceutical drug development to improve the solubility of hydrophobic APIs. Many such polymers used for the parenteral delivery of drugs are non-degradable and can accumulate in tissue or the blood stream for prolonged periods of time. This is especially problematic for large molecular weight polymers above the renal threshold, and even those below as a portion will be above the threshold as polymers have a certain degree of polydispersity (see: Seymour, L. et al., *J. Biomed. Mater. Res.*, 1987, 21(11), 1341-1358).

Nippon Kayaku has developed NK012, a micellular nanoparticle formulation of SN-38 entrapped in a synthetic block polymer comprising poly(ethylene glycol)-poly(glutamic acid) (PEG-PGA) (see: Koizumi, F. *Cancer Res.*, 2006, 66(20), 10048-10056). Intezyne Technologies has developed IT-141, another micellular formulation of SN-38 utilizing a PEG-(poly amino acid) (PAA) triblock copolymer stabilized by glutamic acid derived hydroxamates coordinated with iron(III) (see: Carie, A. et al. *J. Drug Delivery* 2011, Article ID 869027). Both of these formulations utilize PEG-containing copolymers which are constructed from the polymerization of amino acid N-carboxyanhydrides (NCAs) originating from an amine-containing PEG initiator. The preparation of such PEG initiators in not trivial and requires the extremely hazardous polymerization of ethylene oxide. Compounding the problem, even trace impurities in the PEG-initiator can have significant effects on the physical properties of the final PEG-PAA copolymer (see: Vojkovsky, T. et al. *Polymer,* 2016, 105, 72-78; Sill, K. et al. *Biomacromolecules* 2017, 18(6), 1874-1884). Furthermore, the use of PEG-based polymers poses a particular set of concerns as growing evidence of anti-PEG antibodies and kidney-targeting toxicities raises obvious concerns over their use in pharmaceuticals (see: Garay, R. et al., *Expert Opin. Drug Delivery,* 2012, 1319-1323; Yang, Q. et al., *Anal. Chem.* 2016, 88(23), 11804-11812; Wenande, E. et al., *Clin. Exp. Allergy,* 2016, 46(7), 907-922.; Webster, R. DrugMetab. Dispos, 2007, 35(1), 9-16).

Those skilled in the art will recognize the need for a drug product that increases the water-solubility of SN-38 allowing for its administration directly to a patient, without the need for a pro-drug. PAA polymer excipients that fulfils this role, and which does not incorporate potentially harmful, non-biodegradable polymers such as PEG, would be understood as an attractive solution. It will also be recognized that the amount of SN-38 delivered based on the patients UGT1A1 genotype would reduce the probability of neutropenia and diarrhea.

BRIEF SUMMARY OF THE DISCLOSURE

The present disclosure provides a composition comprising SN-38 and a poly(amino acid) block copolymer excipient. Also provided is a composition described herein for use in treating cancer. Also provided herein is a method for treating cancer in a subject in need thereof, comprising administering to the subject a therapeutically effective amount of a composition or a unit dose form described herein. Also provided herein are methods of preparing a composition or a unit dose form described herein.

DETAILED DESCRIPTION OF CERTAIN EMBODIMENTS OF THE DISCLOSURE

1. General Description

As described herein, the present disclosure describes a composition which comprises SN-38 and a poly(amino acid) block copolymer as depicted in Formula I:

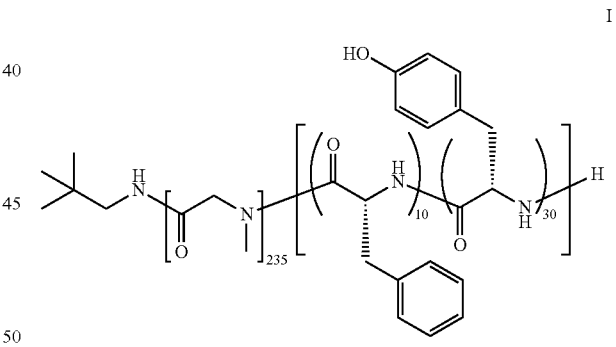

The present disclosure also describes methods for the manufacture of compositions comprising SN-38 and the compound represented by Formula I. Such compositions are pharmaceutically acceptable drug products suitable for administration to human patients.

The present disclosure also describes methods for the treatment of cancers comprising administration of a composition comprising SN-38 and a compound represented by Formula I.

2. Definitions

The following are definitions of various terms used herein to describe the present disclosure and are further illustrated by the embodiments, sub-embodiments, and species disclosed herein. These definitions apply to the terms as they are used throughout this specification unless otherwise indicated in specific instances, either individually or as part of a larger group.

It is understood that the terms "SN-38", "7-ethyl-10-hydroxycamptothecin" refer to (19S)-10,19-diethyl-7,19-dihydroxy-17-oxa-3,13-diazapentacyclo[11.8.0.0$^{2,11}$.0$^{4,9}$.0$^{15,20}$] henicosa-1(21),2,4(9),5,7,10,15(20-heptaene-14,18-dione, and any salts, solvates, or hydrates thereof.

It is understood that the terms "TFS-3", "poly(sarcosine)$_{235}$-block-poly(d-phenylalanine$_{10}$-co-tyrosine$_{30}$)", "PSar$_{235}$-P(dPhe$_{10}$/Tyr$_{30}$)", "poly[Sar$_{235}$]-block-poly-[D-Phe$_{10}$-co-L-Tyr$_{30}$]", and a copolymer represented Formula I, all represent the same compound and can be used interchangeably.

It is understood that the terms "TYN-38" refers to a formulation comprising SN-38, TFS-3, and trehalose wherein the SN-38 is about 10% weight loading of the formulation.

As used herein, the term "block copolymer" refers to a polymer comprising two or more poly(amino acid) portions. As described herein, one or more of the amino acid blocks may be "mixed blocks", meaning that these blocks can contain a mixture of amino acid monomers thereby creating block copolymers of the present disclosure. One skilled in the art will recognize that a monomer repeat unit is defined by parentheses depicted around the repeating monomer unit. The number (or letter representing a numerical range) on the lower right of the parentheses represents the number of monomer units that are present in the polymer chain. In the case where only one monomer represents the block (e.g. a homopolymer), the block will be denoted solely by the parentheses. In the case of a mixed block, multiple monomers comprise a single, continuous block. It will be understood that brackets will define a portion or block. For example, one block may consist of four individual monomers, each defined by their own individual set of parentheses and number of repeat units present. All four sets of parentheses will be enclosed by a set of brackets, denoting that all four of these monomers combine in random, or near random, order to comprise the mixed block. For clarity, the randomly mixed block of [BCADDCBADABCDABC] would be represented in shorthand by [(A)$_4$(B)$_4$(C)$_4$(D)$_4$].

As used herein, "copolymer" refers to a polymer comprising two or more poly(amino acid portions).

As used herein, "weight loading" refers to the ratio of a drug to the total drug product formulation which can include, but is not limited to, drugs, excipients and copolymers. Weight loading is expressed as a weight percentage (% w/w), for example; 20 mg of a drug in a total formulation further comprising 90 mg of a cryoprotectant and 90 mg of a copolymer would be expressed as 10% weight loading, (20/(20+90+90)=10%).

As used herein, "feed ratio" refers to the ratio of drug combined with a copolymer during the manufacturing of a drug product. Feed ratio is expressed as a weight percentage (% w/w), for example; 100 mg of a drug combined with 500 mg of a copolymer (independent of other components) would be expressed as a feed ratio of 20% (100/500=20%). Feed ratio is independent of other components present in the drug product. Thus, a 10% feed ratio may result in a drug product containing 5% drug by weight when other components of the drug product are taken into account. Representative feed ratios include from about 1% to about 50%, from about 5% to about 50%, from about 10% to about 50%, from about 10% to about 40%, from about 15% to about 25%, about 4%, about 5%, about 10%, about 15%, about 20%, about 25%, about 30%, about 35% or about 40%.

As used herein, "high shear mix" or "high shear mixing", refers to dispersing a combination of components into a continuous phase which would normally be immiscible via emulsification, sonication, or microfluidizing.

As used herein, "unit dosage form" or "unit dose form" refers to a physically discrete unit of a formulation appropriate for the subject to be treated. It will be understood, however, that the total daily usage of the compositions of the present disclosure will be decided by the attending physician within the scope of sound medical judgement. The specific effective dose level for any particular subject or organism will depend on a variety of factors including the disorder being treated and the severity of the disorder; activity of specific active agent employed; specific composition employed; age, body weight, general health, sex and diet of the subject; time of administration, and rate of excretion of the specific active agent employed; duration of treatment, drugs/and or additional therapies used in combination or coincidental with specific compound(s) employed and like factors well known in the medical arts.

As used herein, a "drug product" means a therapeutic agent, and one or more excipients selected from, but not limited to, tonicity agents, cryoprotectants, multiblock copolymers, stabilizing agents, antiadherents, binders, coatings, colors, disintegrants, flavors, glidants, lubricants, preservatives, sorbents, sweeteners, and vehicles. As appreciated by those skilled in the art, the amounts of each excipient will depend on the therapeutic agent, the route of administration, the desired biological endpoint, the target cell or tissue.

As used herein, a "cryoprotectant" or "cryoprotective agent" refers to compounds which either prevent freezing or prevent damage, or alteration to other compounds related to freezing. This includes, but is not limited to: sugars, monosaccharides, disaccharides, polyalcohols, amino acids, glycine, polyvinyl pyrrolidine, polyethylene glycol, mannitol, sorbitol, sucrose, glucose, raffinose, sucralose, lactose, trehalose, dextran, and dextrose.

As used herein, a "therapeutically effective amount" means an amount of a substance (e.g. a therapeutic agent, composition, and/or formulation) that elicits a desired biological response. In some embodiments, a therapeutically effective amount of a substance is an amount that is sufficient, when administered as part of a dosing regimen to a subject suffering from or susceptible to a disease, disorder, and/or condition, to treat, slow the progression of, and/or delay the onset of the disease, disorder, and/or condition. As will be appreciated by those of ordinary skill in this art, the effective amount of a substance may vary depending on such factors as the desired biological endpoint, the substance to be delivered, the target cell or tissue, etc. For example, the effective amount of compound in a formulation to treat a disease, disorder, and/or condition is the amount that alleviates, ameliorates, relieves, inhibits, slows the progression of, delays onset of, reduces severity of and/or reduces incidence of one or more symptoms or features of the disease, disorder, and/or condition. In some embodiments, a "therapeutically effective amount" is at least a minimal amount of a compound, or composition containing a compound, which is sufficient for treating one or more symptoms of a disease or disorder associated with proliferative diseases, such as cancer.

The term "subject", as used herein, means a mammal and includes human and animal subjects, such as domestic animals (e.g. horses, dogs, cats, etc.).

The terms "treat" or "treating," as used herein, refers to partially or completely alleviating, inhibiting, delaying onset of, ameliorating, slowing the progression of and/or relieving a disease or disorder, or one or more symptoms of the disease or disorder. As used herein, the terms "treatment," "treat," and "treating" refer to partially or completely alleviating, inhibiting, delaying onset of, ameliorating, slowing the progression of and/or relieving a disease or disorder, or one or more symptoms of the disease or disorder, as described herein. In some embodiments, treatment may be administered after one or more symptoms have developed. In some embodiments, the term "treating" includes slowing or halting the progression of a disease or disorder. In other embodiments, treatment may be administered in the absence of symptoms. For example, treatment may be administered to a susceptible individual prior to the onset of symptoms (e.g. in light of a history of symptoms and/or in light of genetic or other susceptibility factors). Treatment may also be continued after symptoms have resolved, for example to prevent or delay their recurrence. Thus, in some embodiments, the term "treating" includes preventing relapse or recurrence of a disease or disorder.

"Metastatic," used herein to describe cancer, refers to cancer that has spread from the part of the body where it started to other parts of the body.

"Locally advanced," used herein to describe cancer, refers to cancer that has grown outside the organ it started in but has not yet spread to distant parts of the body.

A subject is said to have "failed" a therapy, or the term "failure" in the context of a previous treatment, as used herein means the subject relapses from the therapy, or is resistant or refractory to the therapy (e.g., progresses following or while on the therapy). For example, treatment of a subject having breast cancer that has not metastasized or advanced locally may not prevent the breast cancer from metastasizing or advancing locally. If the treatment does not prevent the breast cancer from metastasizing or advancing locally, and the breast cancer metastasizes and/or advances locally, the subject is said to have failed the treatment because the subject's cancer progressed following or while on the treatment. In another example, a subject previously diagnosed with metastatic or locally advanced breast cancer may be treated with a therapy for such cancer, but fail to respond to the therapy. This subject, too, is said to have failed the therapy because the subject is resistant or refractory to the therapy. Similarly, a subject that experiences remission following a therapy, but subsequently relapses, is considered to have failed the prior therapy.

"Prior therapy," as used herein, refers to any therapy given before the referenced therapy for a disease or condition. When a prior therapy includes drug(s), the referenced or subsequent therapy comprises one or more drugs that are different from the drug(s) of the prior therapy. In some embodiments, the subsequent therapy is a second-line therapy (i.e., the second therapy given for a disease or condition). In some embodiments, the subsequent therapy is a third-line therapy (i.e., the third therapy given for a disease or condition). In some embodiments, the subsequent therapy is a fourth-line therapy (i.e., the fourth therapy given for a disease or condition).

The term "parenteral" as used herein includes subcutaneous, intravenous, intramuscular, intra-articular, intra-synovial, intrasternal, intrathecal, intrahepatic, intralesional and intracranial injection or infusion techniques. Preferably, the compositions are administered intraperitoneally or intravenously. Sterile injectable forms of the compositions of this disclosure may be aqueous or oleaginous suspension. These suspensions may be formulated according to techniques known in the art using dispersing or wetting agents and suspending agents. The sterile injectable preparation may also be a sterile injectable solution or suspension in a non-toxic parenterally acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium.

The term "about" when referring to a measurable value such as an amount, a temporal duration, and the like, refers to variations of ±20% or in some instances 10%, or in some instances ±5%, or in some instances ±2%, or in some instances ±1%, or in some instances ±0.1% from the specified value, as such variations are appropriate to perform the present disclosures.

3. Description of Exemplary Embodiments 3.1 Drug Product

In some embodiments the present disclosure provides a drug product comprising a formulation or composition described herein.

In some embodiments the present disclosure provides a composition comprising SN-38, and TFS-3.

In some embodiments the present disclosure provides a composition comprising SN-38, TFS-3, and a cryoprotectant. In a preferred embodiment, said cryoprotectant is trehalose.

The weight loading of SN-38 in the drug product of the present disclosure can have effects on reconstitution properties, stability, and manufacturing. In some embodiments the disclosure is directed to drug products with SN-38 weight loadings from about 0.1% to about 30%. In other embodiments the present disclosure is directed to drug products with SN-38 weight loadings from about 5% to about 15%.

One embodiment of the present disclosure provides a composition comprising SN-38, TFS-3, and a cryoprotectant,
  wherein:
    the SN-38 is about 1% by weight to about 30% by weight of the composition,
    the TFS-3 is about 10% by weight to about 90% by weight of the composition,
    and the cryoprotectant is about 10% by weight to about 90% by weight of the composition.

One embodiment of the present disclosure is directed to a composition comprising SN-38, TFS-3, and a cryoprotectant,
  wherein:
    the SN-38 is about 5% by weight to about 15% by weight of the composition,
    the TFS-3 is about 30% by weight to about 60% by weight of the composition,
    and the cryoprotectant is about 30% by weight to about 60% by weight of the composition.

One embodiment of the present disclosure is directed to a composition comprising SN-38, TFS-3, and trehalose,
  wherein:
    the SN-38 is about 1% by weight to about 30% by weight of the composition,
    the TFS-3 is about 10% by weight to about 90% by weight of the composition,
    and the trehalose is about 10% by weight to about 90% by weight of the composition.

One embodiment of the present disclosure is directed to a composition comprising SN-38, TFS-3, and trehalose,
  wherein:

the SN-38 is about 5% by weight to about 15% by weight of the composition, the TFS-3 is about 30% by weight to about 60% by weight of the composition, and the trehalose is about 30% by weight to about 60% by weight of the composition.

3.2 Unit Dosage Form

In some embodiments the present disclosure provides a unit dosage form comprising a formulation or composition described herein.

In some embodiments, the present disclosure is directed to pharmaceutical packs and/or kits comprising compositions described herein, or a unit dosage form comprising a provided composition, and a container (e.g. foil, or plastic package, or other suitable container). Optionally instructions for use are additionally provided in such kits.

Composition of the present disclosure can be provided as a unit dosage form. In some embodiments, a vial comprising SN-38 and TFS-3 is a unit dosage form. In some embodiments, a vial comprising SN-38, TFS-3, and a cryoprotectant is a unit dosage form. In a preferred embodiment, a vial comprising SN-38, TFS-3, and trehalose is a unit dosage form.

One embodiment of the present disclosure provides a composition comprising SN-38, TFS-3, and a cryoprotectant, wherein:

the SN-38 is present in about 6 mg to about 150 mg, the TFS-3 is present in about 27 mg to about 675 mg, and the cryoprotectant is present in about 27 mg to about 675 mg.

One embodiment of the present disclosure provides a composition comprising SN-38, TFS-3, and a cryoprotectant, wherein:

the SN-38 is present in about 15 mg to about 60 mg, the TFS-3 is present in about 67 mg to about 270 mg, and the cryoprotectant is present in about 67 mg to about 270 mg.

One embodiment of the present disclosure provides a composition comprising SN-38, TFS-3, and trehalose, wherein:

the SN-38 is present in about 6 mg to about 150 mg of the composition, the TFS-3 is present in about 27 mg to about 675 mg of the composition, and the trehalose is present in about 27 mg to about 675 mg of the composition.

One embodiment of the present disclosure provides a composition comprising SN-38, TFS-3, and trehalose, wherein:

the SN-38 is present in about 15 mg to about 60 mg, the TFS-3 is present in about 67 mg to about 270 mg, and the trehalose is present in about 67 mg to about 270 mg.

In some embodiments, the present disclosure can be provided as a unit dosage form. For example, a vial comprising SN-38, TFS-3, and trehalose is a unit dosage form that may be provided. In Some embodiments the unit dosage form is selected from those in Table 2:

TABLE 2

Pharmaceutical Components of Unit Dosage Form

| Component | Function | Amount/vial |
|---|---|---|
| SN-38 | Active | 27-33 mg |
| TFS-3 | Excipient | 108-162 mg |
| Trehalose | Cryoprotectant | 108-162 mg |

In a preferred embodiment, the unit dosage form is depicted in Table 3:

TABLE 3

Pharmaceutical Components of Unit Dosage Form

| Component | Function | Weight % | Amount/vial |
|---|---|---|---|
| SN-38 | Active | 10% | 30 mg |
| TFS-3 | Excipient | 45% | 135 mg |
| Trehalose | Cryoprotectant | 45% | 135 mg |

In some embodiments, the unit dosage forms of the present disclosure are provided in a sealed container. In some embodiments, the unit dosage forms of the disclosure are provided as lyophilized powders. In some embodiments, the unit dosage forms of the disclosure are provided as an infusion solution. In some embodiments, the infusion solution comprises a vehicle selected from water, 1,3-butanediol, Ringer's solution or an isotonic sodium chloride solution.

In some embodiments, the unit dosage forms contemplated by the disclosure are provided as a kit. The kit may comprise a first and a second container, wherein the first container comprises a composition as described herein, and the second container comprises a vehicle as described herein. In some embodiments, the first container comprises a composition as described herein as a lyophilized dry powder. The kits of the disclosure may allow for the dissolution of the lyophilized compositions described herein immediately prior to the administration of those compositions to a subject in need thereof.

In some embodiments, the compositions of the disclosure are formulated with a pharmaceutically acceptable carrier. Pharmaceutically acceptable carriers that may be used in the compositions of the disclosure include, but are not limited to, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene glycol and wool fat. The compositions of the disclosure may be formulated for administration in any convenient way for use in human medicine.

The compositions of the disclosure may be formulated for a variety of administration methods. Administration methods contemplated by the disclosure include topical, systemic, or local administration. For example, therapeutic compositions of the disclosure may be formulated for parenteral administration (e.g., subcutaneous, intravenous, intramuscular, intra-articular, intra-synovial, intrasternal, intrathecal, intrahepatic, intralesional and intracranial injection or infusion techniques), administration by inhalation or insufflation (either through the mouth or the nose) or oral, buccal, sublingual, transdermal, or nasal administration. The compositions described herein may be formulated as part of an implant or device, or formulated for slow or extended release.

In certain embodiments of the disclosure, the compositions are formulated for oral administration, e.g., in the form of capsules, cachets, pills, tablets, lozenges (using a flavored basis, usually sucrose and acacia or tragacanth), powders, granules, or as a solution or a suspension in an aqueous or non-aqueous liquid, or as an oil-in-water or water-in-oil liquid emulsion, or as an elixir or syrup, or as pastilles (using an inert base, such as gelatin and glycerin, or sucrose and acacia) and the like.

In solid dosage forms for oral administration (capsules, tablets, pills, dragees, powders, granules, and the like), the compositions of the disclosure may be mixed with one or more pharmaceutically acceptable carriers, such as sodium citrate or dicalcium phosphate, and/or any of the following: (1) fillers or extenders, such as starches, lactose, sucrose, glucose, mannitol, and/or silicic acid; (2) binders, such as, for example, carboxymethylcellulose, alginates, gelatin, polyvinyl pyrrolidone, sucrose, and/or acacia; (3) humectants, such as glycerol; (4) disintegrating agents, such as agar-agar, calcium carbonate, potato or tapioca starch, alginic acid, certain silicates, and sodium carbonate; (5) solution retarding agents, such as paraffin; (6) absorption accelerators, such as quaternary ammonium compounds; (7) wetting agents, such as, for example, cetyl alcohol and glycerol monostearate; (8) absorbents, such as kaolin and bentonite clay; (9) lubricants, such a talc, calcium stearate, magnesium stearate, solid polyethylene glycols, sodium lauryl sulfate, and mixtures thereof; and (10) coloring agents. In the case of capsules, tablets and pills, the pharmaceutical compositions may also comprise buffering agents. Solid compositions of a similar type may also be employed as fillers in soft and hard-filled gelatin capsules using such excipients as lactose or milk sugars, as well as high molecular weight polyethylene glycols and the like.

In some embodiments, the drug products of this disclosure are formulated as liquid dosage forms for oral administration. Liquid dosage forms for oral administration include pharmaceutically acceptable emulsions, microemulsions, solutions, suspensions, syrups and elixers. The liquid dosage forms may contain inert diluents commonly used in the art such as water or other solvents, solubilizing agents and emulsifiers, such as ethanol, isopropyl alcohol, ethyl carbonate, ethyl acetate, benzyl alcohol, benzyl benzoate, propylene glycol, 1,3-butyline glycol, oils (e.g., cottonseed, groundnut, corn, germ, olive, castor and sesame oils), glycerol, tetrahydrofuryl alcohol, polyethylene glycols and fatty acid esters or sorbitan and mixtures thereof. The oral compositions can also include adjuvants such as wetting agents, emulsifying and suspending agents, sweetening, flavoring, coloring, perfuming and preservative agents.

In certain embodiments, the compositions of the disclosure are formulated for parenteral administration. As an example, the compositions of the disclosure can be formulated for parenteral administration by further including one or more pharmaceutically acceptable sterile isotonic aqueous or non-aqueous solutions, dispersions, suspensions or emulsions, or sterile powders which may be reconstituted into sterile injectable solutions or dispersions just prior to use. The compositions for parenteral administration may contain antioxidants, buffers, bacteriostats, and/or solutes which render the formulation isotonic with the blood of the intended recipient or suspending or thickening agents. Examples of suitable aqueous and non-aqueous vehicles which may be employed in the pharmaceutical compositions of the disclosure include water, Ringer's solution, an isotonic salt solution, ethanol, polyols (such as 1,3-butanediol, glycerol, propylene glycol, polyethylene glycol, and the like), and suitable mixtures thereof, vegetable oils, such as olive oil, and injectable organic esters, such as ethyl oleate. In a preferred embodiment, the compositions of the disclosure are intended for parenteral administration, and further comprise a vehicle selected from water, 1,3-butanediol, Ringer's solution or an isotonic sodium chloride solution.

As described herein, the compositions of the disclosure may be administered for slow, controlled or extended release. The term "extended release" is widely recognized in the art of pharmaceutical sciences and is used herein to refer to a controlled release of an active compound or agent from a dosage form to an environment over (throughout or during) an extended period of time, e.g. greater than or equal to one hour. An extended release dosage form will release drug at substantially constant rate over an extended period of time or a substantially constant amount of drug will be released incrementally over an extended period of time. The term "extended release" used herein includes the terms "controlled release," "prolonged release," "sustained release," "delayed release," or "slow release" as these terms are used in the pharmaceutical sciences. In some embodiments, the extended release dosage is administered in the form of a patch or a pump.

3.3 Process of Manufacturing

In certain embodiments, the present disclosure provides methods for preparing drug products comprising SN-38 and TFS-3.

In one aspect, the disclosure is directed to a method for preparing a sterile, lyophilized drug product comprising SN-38 and TFS-3. This drug product would be suitable for administration to a patient. One embodiment of the disclosure provides a method for preparing a sterile, lyophilized drug product comprising SN-38, TFS-3, and a cryoprotective agent. The general method for providing said drug product comprises the steps of preparing a solution of a cryoprotectant and TFS-3 in water. Preparing a solution of SN-38 in an organic solvent. Adding said SN-38 solution to said solution of a cryoprotectant and TFS-3 while shear mixing with a homogenizer to produce a homogenous emulsion. Processing said homogenous emulsion through a high shear mixer (e.g. microfluidizer). Processing the high shear mixer extruded solution via tangential flow filtration against an aqueous solution of cryoprotectant. Sterile filtering the resulting solution (e.g. aseptic filtration), filing of vials under sterile conditions, and lyophilization under sterile conditions. Suitable cryoprotective agents include, but are not limited to: sugars, monosaccharides, disaccharides, polyalcohols, amino acids, glycine, polyvinyl pyrrolidine, polyethylene glycol, mannitol, sorbitol, sucrose, glucose, raffinose, sucralose, lactose, trehalose, dextran, and dextrose. In a preferred embodiment the cryoprotectant is trehalose.

In some embodiments, the disclosure is directed to a method of preparing a unit dosage form comprising:
a) dissolving SN-38, or a pharmaceutically acceptable salt thereof, a copolymer of Formula I and, optionally, a cryoprotectant, in an aqueous solution, thereby forming a mixed solution;
b) processing the mixed solution through a high shear mixer, thereby forming a high shear mixed solution; and
c) optionally lyophilizing the high shear mixed solution.

In some embodiments, the disclosure is directed to a method of preparing a unit dosage form comprising:
a) dissolving SN-38, or a pharmaceutically acceptable salt thereof, in an organic solvent, thereby forming an SN-38 solution;
b) dissolving a copolymer of Formula I and, optionally, a cryoprotectant, in an aqueous solution, thereby forming a copolymer solution;
c) mixing the SN-38 solution and the copolymer solution, thereby forming a mixed solution;
d) processing the mixed solution through a high shear mixer, thereby forming a high shear mixer solution;
e) filtering the high shear mixer solution, thereby forming a filtered solution; and
f) optionally lyophilizing the filtered solution.

In some embodiments, the disclosure is directed to a method of preparing a unit dosage form comprising:
a) dissolving SN-38, or a pharmaceutically acceptable salt thereof, in an organic solvent, thereby forming an SN-38 solution;
b) dissolving a copolymer of Formula I and, optionally, a cryoprotectant, in an aqueous solution, thereby forming a copolymer solution;
c) mixing the SN-38 solution and the copolymer solution, thereby forming a mixed solution;
d) processing the mixed solution through a high shear mixer, thereby forming a high shear mixer solution;
e) processing the high shear mixer solution with a diafiltration system, thereby forming a diafiltered solution;
f) filtering the diafiltered solution, thereby forming a filtered solution; and
g) optionally lyophilizing the filtered solution.

3.4 Methods of Use

Compositions comprising irinotecan, a pro-drug of SN-38, are known to be useful for the treatment of patients with cancer, alone or in combination with other therapeutic agents and/or therapies. Such patients include those who have previously been treated for cancer, and those who have not previously been treated for cancer.

The compositions of the present disclosure comprise SN-38 and TFS-3 and are useful in the treatment of a variety of cancers and other proliferative diseases.

The compositions of the present disclosure are useful in the treatment a cancer including, but not limited to, the following: multiple myeloma, breast, ovary, cervix, prostate, testis, genitourinary tract, esophagus, larynx, glioblastoma, neuroblastoma, stomach (gastric), skin, keratoacanthoma, lung, epidermoid carcinoma, large cell carcinoma, small cell carcinoma, lung, bone, colon, thyroid, adenoma, pancreas, adenocarcinoma, thyroid, follicular carcinoma, undifferentiated carcinoma, papillary carcinoma, seminoma, melanoma (including uveal melanoma) sarcoma, bladder carcinoma, liver carcinoma (e.g., hepatocellular carcinoma (HCC)) and biliary passages, kidney carcinoma, myeloid disorders, lymphoid disorders, Hodgkin's disease, hairy cells, tumors of mesenchymal origin including fibrosarcoma and rhabdomyosarcoma, buccal cavity and pharynx (oral), lip, tongue, mouth, pharynx, small intestine, colorectal carcinoma, large intestine, rectum, brain and central nervous system, endometrial, multiple myeloma (MM), prostate, acute myeloid leukemia (AML), and leukemia.

In a preferred embodiment, the caner is colorectal.
In a preferred embodiment the cancer is non-small cell lung carcinoma (NSCLC).
In a preferred embodiment the cancer is small cell lung carcinoma (SCLC).
In a preferred embodiment the cancer is adenocarcinoma of the pancreas.
In a preferred embodiment the cancer is ovarian.
In a preferred embodiment the cancer is gastric.
In a preferred embodiment the cancer is esophageal.
In a preferred embodiment the cancer is breast.

In some embodiments the cancer is a locally advanced cancer. In some embodiments the cancer is metastatic. In some embodiments the cancer is reoccurring. In some embodiments the cancer is relapsed. In some embodiments the cancer is refractory.

In a preferred embodiment the compositions of the disclosure are useful in combination with 5-fluorouracil and leucovorin for the treatment of metastatic colorectal cancer.

In a preferred embodiment the compositions of the disclosure are useful as a single agent for the treatment of metastatic colorectal cancer after failure of a 5-fluorouracil-based chemotherapy.

In a preferred embodiment the compositions of the disclosure are useful in combination with one or more therapeutic agents for the treatment of patients with metastatic adenocarcinoma of the pancreas after disease progression following gemcitabine-based therapy. In some embodiments, the therapeutic agent is selected from 5-fluorouracil or leucovorin.

The present disclosure provides compositions comprising a multiblock copolymer of Formula I and SN-38 that may be administered to a patient in need thereof. Routes of administration include, but are not limited to, parenterally, orally, sublingually, buccally, rectally, vaginally, by the ocular route, by the otic route, nasally, inhalation, nebulization, cutaneously, subcutaneously, topically, systemically, or transdermally. In a preferred embodiment, the route of administration is intravenous. In another preferred embodiment the route of administration is via a central venous catheter. In another preferred embodiment the route of administration is via a peripheral venous catheter.

In some embodiments, the present disclosure is directed to a method for treating, stabilizing, or lessening the severity or progression of one or more proliferative diseases (e.g. cancer), wherein the method comprises administering to a patient in need thereof a pharmaceutically acceptable composition comprising a copolymer of Formula I and SN-38 wherein the treatment is metronomic.

In some embodiments, the present disclosure is directed to a method for treating, stabilizing, or lessening the severity or progression of one or more proliferative diseases (e.g. cancer) in a subject in need thereof, wherein the method comprises:
a) measuring the UGT1A1 genotype of the subject;
b) identifying if the subject has a UGT1A1 *1/*1, UGT1A1 * 1/*28, or UGT1A1 *28/*28 genotype; and
c) administering SN-38 to the subject an amount appropriate to the UGT1A1 genotype.

In some embodiments, SN-38 is administered to the subject as a pharmaceutically acceptable composition as described herein, comprising a copolymer of Formula I and SN-38 at a dose specific for the genotype of the patient.

In some embodiments, the present disclosure is directed to a method for treating, stabilizing, or lessening the severity or progression of one or more proliferative diseases (e.g. cancer), wherein the method comprises administering to a patient in need thereof a pharmaceutically acceptable composition comprising a copolymer of Formula I and SN-38 wherein the treatment is given in a single, or on a repeating dosing schedule. In some embodiments, the composition comprising a copolymer of Formula I and SN-38 is administered at least one of 1×, 2×, 3×, 4×, 5×, 6×, or 7× a week. In some embodiments, the composition comprising a copolymer of Formula I and SN-38 is administered at an interval of about 1 day, 2 days, 3 days, 4 days, 5 days, 6 days, 7 days, 8 days, 9 days, 10 days, 11 days, 12 days, 13 days, 14 days, 15 days, 16 days, 17 days, 18 days, 19 days, 20 days, 21, days 22 days. 23 days, 24 days, 25 days, 26 days, 27 days, 28 days. In some embodiments, the composition comprising a copolymer of Formula I and SN-38 is administered over a period of about any of 1, 2, 3, 4, 5, 6, 7, 8, 9, 10, 11, 12, 18, 24, or 36 months. In a preferred embodiment the composition comprising a copolymer of Formula I and SN-38 is administered on day 1, and day 15 of a 28-day cycle. In another preferred embodiment the composition comprising a copolymer of Formula I and SN-38 is administered on day 1, day 8, and day 15 of a 28-day cycle. In another preferred embodiment the composition comprising a copolymer of Formula I and SN-38 is administered on day 1 of a 21-day cycle.

In some embodiments, the disclosure is directed to a method for treating, stabilizing, or lessening the severity or progression of one or more proliferative diseases (e.g. cancer), wherein the method comprises administering to a patient in need thereof a pharmaceutically acceptable composition comprising a copolymer of Formula I and SN-38 wherein the administration is performed over about 10 to about 90 minutes. In a preferred embodiment, the administration is performed over about 30 minutes. In another preferred embodiment, the administration is performed over about 60 minutes.

In some embodiments, the disclosure is directed to a method for treating, stabilizing, or lessening the severity or progression of one or more proliferative diseases (e.g. cancer), wherein the method comprises administering to a patient in need thereof a pharmaceutically acceptable composition comprising a copolymer of Formula I and SN-38 wherein the dose of SN-38 is about 5 to about 100 mg/m$^2$ body surface area. In a preferred embodiment the dose of SN-38 is about 20 to about 50 mg/m$^2$ body surface area.

In some embodiments, the disclosure is directed to a method for treating, stabilizing, or lessening the severity or progression of one or more proliferative diseases (e.g. cancer), wherein the method comprises administering to a patient in need thereof an effective amount of a pharmaceutically acceptable composition comprising a copolymer of Formula I and SN-38 in combination with one or more therapeutic agents. In some embodiments, the composition comprising a copolymer of Formula I and SN-38 with one or more therapeutic agents are administered simultaneously. In some embodiments, the composition comprising a copolymer of Formula I and SN-28 with one or more therapeutic agents are administered sequentially. In some embodiments, the therapeutic agent is an antimetabolite. In a preferred embodiment, the antimetabolite is 5-fluorouracil. In another preferred embodiment, the antimetabolite is leucovorin. In a preferred embodiment, 5-fluorouracil is administered at about 100 to about 2400 mg/m$^2$ body surface area. In another preferred embodiment, leucovorin is administered at about 20 to about 400 mg/m$^2$ body surface area In some embodiments, the present disclosure provides an infusion solution comprising about 0.01 mg/mL to about 150 mg/mL SN-38.

EXEMPLIFICATION

In order for the disclosure to be more fully understood, the following examples are set forth. It will be understood that these examples are for illustrative purposes only and are not to be construed as limiting this disclosure in any manner.

Analytical Methods

The following analytical methods were utilized to characterize the compounds of the present disclosure.

SN-38 HPLC Method—Assay and identity of SN-38 was determined by high pressure liquid chromatography with UV detection at 265 nm. The column utilized was a Phenomenex Gemini® 5 μm C18 (110 Å, 250×4.6 mm) at ambient temperature. The mobile phase consisted of a 70:30 (v/v) mixture of 10 mM sodium phosphate with 0.1% (v/v) triethylamine, pH 3.5 and acetonitrile. SN-38 drug product samples and standards were prepared by dissolving the material in a 7:3 (v/v) mixture of acetonitrile and DMSO. Separation was achieved with a flow rate of 1.5 mL/min for a total run time of 8 minutes.

SN-38 Weigh Loading Analysis—Weight loading was determined by comparing a standard curve of SN-38 to a known concentration of drug product by HPLC analysis. Standards were prepared by dissolving SN-38 in a 7:3 (v/v) mixture of acetonitrile and DMSO at concentrations of 50, 100, 200, 300, and 400 μg/mL. SN-38 drug product samples were prepared by dissolving the material in a 7:3 (v/v) mixture of acetonitrile and DMSO at a concentration between 1-4 mg/mL depending on the weight loading. The amount of SN-38 in the drug product is then converted to weight percentage of the total based on the known quantity of drug product.

Example 1—Preparation of SN-38 Drug Product with 15% SN-38 Feed

Trehalose (8.0 g) was dissolved in 400 mL of water before the addition of 2.0 g of TFS-3 (Sar$_{235}$[D-Phe$_{10}$-co-Tyr$_{30}$]) to produce a solution of 20 mg/mL trehalose and 5 mg/mL TFS-3. The resulting solution was stirred for 1 hour before filtering through a 0.5 μm polypropylene filter. Separately, a solution of SN-38 was prepared by dissolving 281 mg in 3.75 mL of DMSO, with the assistance of heat, to produce a stock solution of 75 mg/mL. While shear mixing 375 mL of the polymer/trehalose solution with a homogenizer at 10,000 RPM, the SN-38 stock solution was added, and the mixing was continued for 1 minute. The resulting homogenous emulsion was processed with two passes through a microfluidizer with an inlet pressure of 100 PSI and an operating pressure of approximately 25,000 PSI through an auxiliary processing chamber followed by a 50 μm X interaction chamber with the outlet tube cooled in an ice-water bath. The extruded solution was then diafiltered against 2.5 L of 20 mg/mL trehalose using a tangential flow filtration system equipped with a mPES hollow fiber filter (10 kDa MWCO, 790 cm$^2$ surface area) at a flow rate of 300 mL/min. The solution was then concentrated to ~¼ the original volume such that the final polymer concentration was ~20 mg/mL. The formulation solution was then filtered through a 0.2 μm PES filter with a surface area of 20 cm$^2$. The filtered solution was frozen at −80° C. and lyophilized for 2 days. This yielded the drug formulation as a fragmented, slightly yellow cake with an SN-38 weight loading of 5.73%.

Example 2—Preparation of SN-38 Drug Product with 20% SN-38 Feed

Using the general method of Example 1 with the following exception: a total of 5.0 mL of the SN-38 solution (75 mg/mL) was homogenized with 375 mL of the polymer/trehalose solution. This yielded the drug product as a fragmented, slightly yellow cake with an SN-38 weight loading of 7.54%

Example 3—Preparation of SN-38 Drug Product with 25% SN-38 Feed

Using the general method of Example 1 with the following exception: a total of 6.25 mL of the SN-38 solution (75 mg/mL) was homogenized with 375 mL of the polymer/trehalose solution. This yielded the drug product as a fragmented, slightly yellow cake with an SN-38 weight loading of 9.35%

Example 4—Preparation of SN-38 Drug Product with 30% SN-38 Feed

Using the general method of Example 1 with the following exception: a total of 7.5 mL of the SN-38 solution (75 mg/mL) was homogenized with 375 mL of the polymer/trehalose solution. This yielded the drug product as a fragmented, slightly yellow cake with an SN-38 weight loading of 11.64%.

Example 5—Preparation of SN-38 Drug Product with 40% SN-38 Feed

Using the general method of Example 1 with the following exception: a total of 10.0 mL of the SN-38 solution (75 mg/mL) was homogenized with 375 mL of the polymer/trehalose solution. This yielded the drug product as a fragmented, yellow cake with an SN-38 weight loading of 14.80%

Example 6—Preparation of $Sar_{235}$-b-p-[D-$Phe_{10}$-co-L-$Tyr_{30}$] (TFS-3)

A jacketed round-bottom flask equipped to a circulating isopropanol/water bath was cooled to 20° C. prior to the addition of sarcosine N-carboxyanhydride (15.0 g, 130.5 mmol, 235 equiv.), followed by N,N-dimethylformamide (75 mL). The mixture was stirred for <30 seconds before the addition of neopentylamine (1.85 mL of 300 mM in DMF, 48.4 mg, 0.555 mmol, 1 equiv.). The reaction vessel was wrapped in aluminum foil to prevent exposure to light. After 15-20 mins, the reactions started to change from the initial clear and colorless solution to a light orange color that continues to intensify as the reaction proceeds. IR was used to monitor the reaction progression via disappearance of the Sar NCA carbonyl stretches at ~1850 and 1778 $cm^{-1}$, with the latter being the preferred wavenumber to monitor. The next day, after a total of 22 h the reaction was complete. The circulating bath temperature was increased to 25° C. prior to the addition of D-phenylalanine N-carboxyanhydride (1.06 g, 5.55 mmol, 10 equiv.) and L-tyrosine N-carboxyanhydride (3.45 g, 16.7 mmol, 30 equiv.). Additional DMF (~5 mL) was used to rinse down the sides of the funnel and reaction vessel. Significant $CO_2$ gas formation was observed shortly after the reaction was initiated. IR was used to monitor the reaction progression via disappearance of the D-Phe NCA and L-Tyr NCA carbonyl stretches at ~1847 and 1786 $cm^{-1}$, with the latter being the preferred wavenumber to monitor. As the reaction proceeds, the color changed from a clear bright orange to a clear yellow-orange solution that was apparent after only a few hours. The reaction was complete after a total of 30 h. The reaction mixture (total of ~100 mL) was transferred to a beaker and fitted with an overhead stirrer. While vigorously stirring, ethyl acetate (400 mL, 4 volumes) was added to precipitate the product. The solids were collected via filtration into a medium fritted glass funnel, and then the semi-dry material was transferred back to the original precipitation beaker along with additional EtOAc (200 mL, 2 volumes) and slurried with vigorous stirring for 20 mins. The solids were collected in the same glass funnel and washed with additional EtOAc (100 mL, 1 volume) once more. The product was dried in a vacuum oven at 90-100° C. for 2 days to yield 11.3 g (87.9%) of the title compound as a fine off-white powder.

$^1$H NMR (DMSO-$d_6$) δ 9.3-9.0 (28H), 8.5-7.8 (45H), 7.4-6.4 (170H), 4.6-3.6 (784H), 3.2-2.5 (1326H), 1.9 (5H), 1.2-1.1 (6H), 0.9-0.8 (14H); GPC (DMF, 50 mM LiBr) Mn=18.1 kDa, Mp=19.3 kDa, PDI=1.07.

The invention claimed is:
1. A composition comprising SN-38 and a copolymer of Formula I:

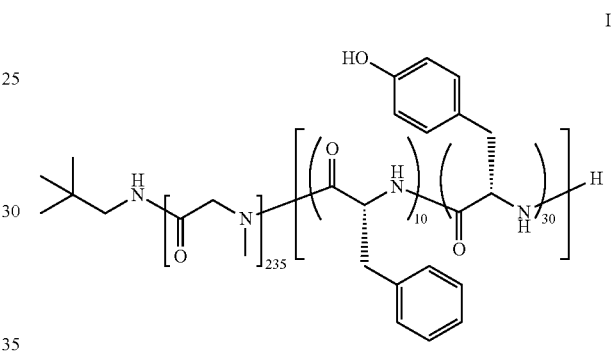

2. The composition according to claim 1, further comprising a cryoprotectant.
3. The composition according to claim 1, wherein the composition comprises:
   from about 1% by weight to about 30% by weight of SN-38; and
   from about 10% by weight to about 90% by weight of a copolymer according to Formula I.
4. The composition according to claim 3, wherein the composition comprises:
   from about 5% by weight to about 15% by weight of SN-38; and
   from about 30% by weight to about 60% by weight of a copolymer according to Formula I.
5. The composition according to claim 4, wherein the composition comprises:
   from about 10% 2% by weight of SN-38; and
   from about 45% 2% by weight of a copolymer according to Formula I.
6. The composition according to claim 2, wherein the composition comprises:
   from about 1% by weight to about 30% by weight of SN-38;
   from about 10% by weight to about 90% by weight of a copolymer according to Formula I; and
   from about 10% by weight to about 90% by weight of a cryoprotectant.
7. The composition according to claim 6, wherein the composition comprises:
   from about 5% by weight to about 15% by weight of SN-38;

from about 30% by weight to about 60% by weight of a copolymer according to Formula I; and from about 30% by weight to about 60% by weight of a cryoprotectant.

8. The composition according to claim 7, wherein the composition comprises:

from about 10% 2% by weight of SN-38;

from about 45%+10% by weight of a copolymer according to Formula I; and from about 45%+10% by weight a cryoprotectant.

9. The composition according to claim 2, wherein the cryoprotectant is glycine, polyvinyl pyrrolidine, polyethylene glycol, mannitol, sorbitol, sucrose, glucose, raffinose, sucralose, lactose, trehalose, dextran, or dextrose.

10. The composition according to claim 9, wherein said cryoprotectant is trehalose.

11. The composition according to claim 1, wherein the composition further comprises one or more therapeutic agents.

12. The composition according to claim 11, wherein the therapeutic agent is 5-fluorouracil or leucovorin.

13. The composition according to claim 1, wherein the composition is in the form of a lyophilized powder.

14. The composition according to claim 1, further comprising a pharmaceutically acceptable vehicle.

15. The composition according to claim 14, wherein the vehicle is one or more of water, 1,3-butanediol, Ringer's solution or an isotonic sodium chloride solution.

16. An infusion solution comprising from about 0.01 mg/mL to about 150 mg/mL SN-38 and a copolymer of Formula I:

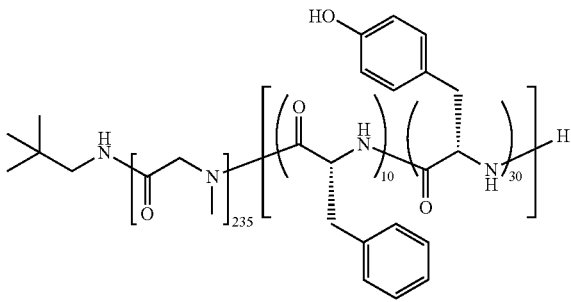

17. The infusion solution according to claim 16, further comprising a cryoprotectant.

18. The infusion solution according to claim 17, wherein the cryoprotectant is selected from glycine, polyvinyl pyrrolidine, polyethylene glycol, mannitol, sorbitol, sucrose, glucose, raffinose, sucralose, lactose, trehalose, dextran, or dextrose.

19. The infusion solution according to claim 18, wherein the cryoprotectant is trehalose.

20. A method of treating a cancer in a subject in need thereof, comprising administering to the subject a composition according to claim 1, or the infusion solution according to claim 16.

21. The method according to claim 20, wherein the cancer is one or more of a locally advanced, a metastatic, a reoccurring, a relapsed or a refractory cancer.

22. The method according to claim 20, wherein the cancer is selected from one or more of colorectal, non-small cell lung carcinoma, small cell lung carcinoma, adenocarcinoma of the pancreas, ovarian, gastric, esophageal, breast cancer, multiple myeloma, breast, ovary, cervix, prostate, testis, genitourinary tract, esophagus, larynx, glioblastoma, neuroblastoma, gastric, skin, keratoacanthoma, lung, epidermoid carcinoma, large cell carcinoma, small cell carcinoma, small cell lung carcinoma, non-small cell lung carcinoma, lung, bone, colon, thyroid, adenoma, pancreas, adenocarcinoma, adenocarcinoma of pancreas, thyroid, follicular carcinoma, undifferentiated carcinoma, papillary carcinoma, seminoma, melanoma, uveal melanoma, sarcoma, bladder carcinoma, liver carcinoma (e.g., hepatocellular carcinoma (HCC)) and biliary passages, kidney carcinoma, myeloid disorders, lymphoid disorders, Hodgkin's disease, hairy cells, tumors of mesenchymal origin including fibrosarcoma and rhabdomyosarcoma, buccal cavity and pharynx, lip, tongue, mouth, pharynx, small intestine, colorectal carcinoma, large intestine, rectum, brain and central nervous system, endometrial, multiple myeloma, prostate, acute myeloid leukemia and leukemia.

23. The method according to claim 20, wherein the cancer is selected from one or more of colorectal, non-small cell lung carcinoma, small cell lung carcinoma, adenocarcinoma of the pancreas, ovarian, gastric, esophageal and breast cancer.

24. The method according to claim 20, wherein the composition is administered in combination with one or more therapeutic agents.

25. The method according to claim 24, wherein the therapeutic agent is 5-fluorouracil or leucovorin.

26. The method according to claim 20, wherein the composition is administered intravenously.

27. The method according to claim 26, wherein the composition is administered via a central venous catheter or via a peripheral venous catheter.

28. The method according to claim 20, wherein the composition is administered metronomically.

29. The method according to claim 28, wherein the composition is administered at least once a month.

30. The method according to claim 28, wherein the composition is administered at least once a week.

31. The method according to claim 20, wherein the duration of the treatment extends over a period ranging from about 1 month to about 36 months.

32. A kit comprising a first container and a second container, wherein:

a) the first container comprises a composition according to claim 1; and b) the second container comprises a pharmaceutically acceptable vehicle.

33. The kit according to claim 32, wherein the pharmaceutically acceptable vehicle is one or more of water, 1,3-butanediol, Ringer's solution or an isotonic sodium chloride solution.

34. A method of preparing a composition of claim 1 comprising:

a) dissolving SN-38, a copolymer of Formula I and, optionally, a cryoprotectant, in an aqueous solution, thereby forming a mixed solution;

b) processing the mixed solution through a high shear mixer, thereby forming a high shear mixer solution; and c) optionally lyophilizing the high shear mixer solution.

35. A method of preparing a composition of claim 1 comprising:

a) dissolving SN-38 in an organic solvent, thereby forming an SN-38 solution;

b) dissolving a copolymer of Formula I and, optionally, a cryoprotectant, in an aqueous solution, thereby forming a copolymer solution;

c) mixing the SN-38 solution and the copolymer solution, thereby forming a mixed solution;
d) processing the mixed solution through a high shear mixer, thereby forming a high shear mixer solution; and
e) optionally lyophilizing the high shear mixer solution.

36. A method of preparing a composition of claim 1 comprising:
   a) dissolving SN-38 in an organic solvent, thereby forming an SN-38 solution;
   b) dissolving a copolymer of Formula I and, optionally, a cryoprotectant, in an aqueous solution, thereby forming a copolymer solution;
   c) mixing the SN-38 solution and the copolymer solution, thereby forming a mixed solution;
   d) processing the mixed solution through a high shear mixer, thereby forming a high shear mixer solution;
   e) processing the high shear mixer solution with a diafiltration system, thereby forming a diafiltered solution;
   f) filtering the diafiltered solution, thereby forming a filtered solution; and
   g) optionally lyophilizing the filtered solution.

* * * * *